(12) United States Patent
Chung et al.

(10) Patent No.: US 6,664,387 B2
(45) Date of Patent: Dec. 16, 2003

(54) EXPRESSION CASSETTE AND PLASMID FOR STRONG CONSTITUTIVE GENE EXPRESSION AND THE USE THEREOF

(75) Inventors: Hwa-Jee Chung, Kwangsan-Gu (KR); Yong Sig Kim, Chongno-Gu (KR); Jeong Woo Cho, Kwangsan-Gu (KR); Chang Ho Chung, Seo-Gu (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 2 days.

(21) Appl. No.: 09/760,731

(22) Filed: Jan. 17, 2001

(65) Prior Publication Data

US 2002/0115850 A1 Aug. 22, 2002

(51) Int. Cl.$^7$ ............................ C12N 15/04; C12N 1/20; C12N 15/63; C12N 15/87; C07H 21/04; A01H 5/00
(52) U.S. Cl. .................. 536/24.1; 536/23.1; 436/252.1; 436/320.1; 800/278; 800/294; 800/306
(58) Field of Search .................... 800/278, 294, 800/298, 306; 536/23.1, 24.1; 435/320.1

(56) References Cited

PUBLICATIONS (Database GenEmbl. Accession No. AC004473. Vysotskaia, V et al, *Arabidopsis thaliana* chromosome 1 BAC TI3D8, complete sequence. Direct submission Jun. 1998. See entire document).*

Rathus, C, et al,Effects of paromoter, intron & enhancer elements on transient gene expression in sugar–cane & carrot prototplasts; Plant Molecular biology, 23: 613–618, 1993.*

Van der Leede–Plegt, LM, et al, Introduction & differential use of various promoters in pollen grains of *Nicotiana glutinosa* & *Lilium longiflorum*.; Plant Cell Reports 11: 20–24., 1992.*

Keith, B, et al,Monocot and dicot pre–mRNAs are processed with different efficienceis in transgenic tobacco; EMBO Journal 5: 2419–2425, 1986.*

Blazquez, Miguel A. et al., "Isolation and molecular characterization of the *Arabidopsis TPS1* gene, encoding trehalose–6–phosphate synthase," The Plant Journal, vol. 13, No. 5, pp. 685–689, 1998.

De Virgilio, Claudio et al., "Disruption of *TPS2*, the gene encoding the 100–kDa subunit of the trehalose–6–phosphate synthase/phosphatase complex in *Saccharomyces cerevisiae*, causes accumulation of trehalose–6–phosphate and loss of trehalose–6–phosphate phosphatase activity," Eur. J. Biochem., vol. 212, pp. 315–323, 1993.

Hammond–Kosack, Kim E. et al., "Plant Disease Resistance Genes," Annu. Rev. Plant Physiol. Plant Mol. Biol., vol. 48, pp. 575–607, 1997.

* cited by examiner

Primary Examiner—Phuong T. Bui
Assistant Examiner—Georgia Helmer
(74) Attorney, Agent, or Firm—Oliff & Berridge, PLC (57) ABSTRACT

The present invention provides isolated nucleic acid constructs comprising a plant strong constitutive promoter operably linked to a heterologous nucleic acid which encodes a desired polypeptide in transgenic plant tissues. Said constructs are capable of conferring the highest expression of the desired polypeptides in plant root tissue and plant leaf tissue when used as a construct for a heterologous coding sequence in chimeric gene. After any chimeric gene can be linked to said construct, the resulting vector can be introduced into plant tissues, thereby intentionally modifying plants and making the resulting plants produce foreign substances therein.

12 Claims, 4 Drawing Sheets

(1 of 4 Drawing Sheet(s) Filed in Color)

SEQUENCE LISTING

<160> NUMBER OF SEQ ID NOS: 5

<210> SEQ ID NO 1
<211> LENGTH: 1013
<212> TYPE: DNA
<213> ORGANISM: Arabidopsis thaliana

<400> SEQUENCE: 1

```
gtgttcattt gatagagtct aaaatcacca cttacattga ctaaccccaa aaatttgtcc      60
taaacactaa tcaatccgaa gattataaaa tgtcgacaaa gaaaataaaa taaaatagga     120
gtctatgagt cgatggaact tatccaacta aactttaata agaatgaacc aaactcaatt     180
ttgtaataat atttaaaata cgtttttact ctctcccaga atatcccatc tctctgattc     240
caattcctcc tctctctctt tcgtctctct acttcgaatt gattgtttta accgccggtg     300
atcggagcaa actctctgac ggtgaccgcc ggtgatcatt ttttgtgaac ttcacttttg     360
gtaagcagct ttgactttg  ttcataatcc ttcacttttc cttttcaatt ttgcttttc      420 ctctgatctg atcttagtta ttaagctgtt gaatcgcatg atcctttctt ctctgattga     480
ttatttctaa tccttcatgg gttttatgac gaatcgtgtc ttagggattg gttttttctg     540
ggttgggttt ctaaatttgt tggtctaaga acagtgaaat tgttgtttca gtgatctcag     600
attctacact tctagtgatt gaactgttat ggaaaattac aaaatatgtg gctctgcttt     660
catttaaatt caatcatcat catctctgct acttgatgat caggtcacct tctctgtgtt     720
ttgtaatctc cataacgtaa gagtttgttt gatattgcaa ttttgaataa gatgattagc     780
atccaatcca atagctgatg ttgaaaccta actctgtaaa gactttaaat ttgttttctc     840
tggctttgtg ctcgttgaag ggtaacctaa agatttgacc tttttgatcc aacacctctc     900
tttttgtact gtaggtgtat aaagcatagt tcgttgggaa cttttttta  cagctttgga     960 gtaactacct ttcatggttt ttggttccaa caatggggtc aaaatcattt gga           1013
```

<210> SEQ ID NO 2
<211> LENGTH: 1943
<212> TYPE: DNA
<213> ORGANISM: Arabidopsis thaliana

<400> SEQUENCE: 2

```
cgacggcatt aacataaacc ataacgctag aaatcttaaa gtattctaat agcctaattt      60
ggtttttatt agaattaaaa ccctacataa tcctggatgt gcgtaacgta gtagttgagc     120
```

-continued

```
tctattctta tacaccagta aagtaaataa ataaaaagaa cagaaaattt catgagcatg    180
cagtagaaaa atcagtcgaa tgttataaaa atagggttac agctaagttc gacgaggtgc    240
tatttcattg gatatcacga aacttgatcg tcaatatgtt ttcttttgt ctttttgtt     300 tttgggtcaa cagatgtata aatgtatttg tatatagctt acatgaagaa cacttggtta    360
gctaaaaaga aaagctaaaa gaaacaaaag aggaggcagc taaaaaacga aaaaagagcc    420
agcattatag atgagcctct tcgtgagcaa gtgagtcgtt tattgtaaga tttgcctctt    480 ctaattttt tctttaaagc cttataattg tatttaaaca aatatcttca taagaaaaaa    540
tatcaaatag atatcaatgt acttttcttt gaaataggat ttcgctatta atccttattt    600
taacattcat ataactgacc aattatattg gtatacagaa aaaaagaatt gtatttgttt    660
ttttcacatt ttagtaaatc tcatttttt ctttctaaat tatgattaat atgaaaatta    720
aaatagaaag tgacatgtcc ttattttaac tccttttatt tcattcattg gtttaatgtt    780
atttacctaa ggatactaat cattggtttt tgaaagataa caataaaaat tcattccaaa    840
catgtggtgc aattatatat aattacaaag tggatagagt atagaactac aaaatggata    900
gagtttagtt ataacaacta atttaaaaaa gtgttcattt gatagagtct aaaatcacca    960
cttacattga ctaaccccaa aaatttgtcc taaacactaa tcaatccgaa gattataaaa   1020
tgtcgacaaa gaaaataaaa taaaatagga gtctatgagt cgatggaact tatccaacta   1080
aactttaata agaatgaacc aaactcaatt ttgtaataat atttaaaata cgtttttact   1140
ctctcccaga atatcccatc tctctgatcc caattcctcc tctctctctt tcgtctctct   1200
acttcgaatt gattgtttta accgccggtg atcggagcaa actctctgac ggtgaccgcc   1260
ggtgatcatt ttttgtgaac ttcacttttg gtaagcagct ttgacttttg ttcataatcc   1320
ttcacttttc cttttcaatt ttgcttttc ctctgatctg atcttagtta ttaagctgtt   1380
gaatcgcatg atcctttctt ctctgattga ttatttctaa tccttcatgg ttttatgac    1440 gaatcgtgtc ttagggattg gttttttctg ggttgggttt ctaaatttgt tggtctaaga   1500
acagtgaaat tgttgtttca gtgatctcag attctacact tctagtgatt gaactgttat   1560
ggaaaattac aaaatatgtg gctctgcttt catttaaatt caatcatcat catctctgct   1620
acttgatgat caggtcacct tctctgtgtt ttgtaatctc cataacgtaa gagtttgttt   1680
gatattgcaa ttttgaataa gatgattagc atccaatcca atagctgatg ttgaaaccta   1740
actctgtaaa gactttaaat ttgttttctc tggctttgtg ctcgttgaag ggtaacctaa   1800
agatttgacc tttttgatcc aacacctctc tttttgtact gtaggtgtat aaagcatagt   1860
tcgttgggaa cttttttta cagctttgga gtaactacct ttcatggttt ttggttccaa   1920
caatggggtc aaaatcattt gga                                          1943
```

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
tccaaatgat tttgaccca t                                               21

<210> SEQ ID NO 4
<211> LENGTH: 21
<212> TYPE: DNA
<213> ORGANISM: Artificial Sequence

```
<220> FEATURE:
<223> OTHER INFORMATION: primer

<400> SEQUENCE: 4
gtgttcattt gatagagtct a                                      21

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cgacggcatt aacataaacc                                        20
```

EXPRESSION CASSETTE AND PLASMID FOR STRONG CONSTITUTIVE GENE EXPRESSION AND THE USE THEREOF

BACKGROUND OF THE INVENTION

The present invention relates to a nucleic acid construct harboring a constitutive non-tissue specific promoter for the higher expression of the desired polypeptide in plant cells and utilization thereof, particularly to a promoter for genes capable of being constitutively expressed in the highest level in transgenic plant root tissues and leaf tissues. The gene expression by said construct is much stronger than that of 35S promoter. The invention is exemplified by the use of Arabidopsis TPS3 promoter for the constitutive regulation of gene expression to produce desirably transformed plants.

For carrying out the crossing, the conventional breeding is problematic in that the genotype to be introduced is limited to one for relative crossing and that it takes a long period of time to obtain the intended hybrids. Using to recent biotechnological development such as genetic engineering technology, however, a desirable gene can be directly introduced into plants, and such system is expected to be capable of overcoming the problems in the conventional breeding. According to the plant genetic engineering, it is also very advantageous in producing plants with improved traits. For improving the resistance to plant diseases, insects and environmental stresses or enhancing the nutritional characteristics of transgenic plants, a strong constitutive promoter which controls expression of the gene should be linked to the desired gene, where it makes the gene be expressed under the control of said promoter. Also, the economical production of biologically active polypeptides is important for the manufacture of pharmaceutical and nutritional formulations and other specialty chemicals in plant biofarming. Recombinant DNA techniques, using transgenic plant cell as expression host generated with a recombinant nucleic acid construct harboring strong constitutive promoter, are particularly useful means for producing large quantities of polypeptides.

Several promoters useful in expressing heterologous genes in plants have already been identified. The most widely used promoter is the 35S promoter from the cauliflower mosaic virus (CaMV35S promoter). The 35S promoter is a strong, constitutive promoter that causes gene expression in all tissues of transgenic plant. Other constitutive promoters that have also been identified include those from the mannopine synthase gene and the nopaline synthase gene of the T-DNA of *Agrobacterium tumefaciens*. For producing recombinant polypeptides that are intended for commercial use, in particular, it is required to obtain a high level of expression of the desired polypeptide from the host cells. Therefore, it requires an expression control signal that is capable of conferring the highest level of strong constitutive expression of the desired polypeptide in plant tissues that maintains expression characteristics. Access to such constitutive promoter would enable the genetic engineering of commercially important crops. The present invention completed this.

Regarding Arabidopsis TPS3 gene, the complete sequence of cDNA of Arabidopsis, which comprises 2,583 bases, has been reported, and the amino acid sequence thereof comprising 861 residues has also been deduced (see GenBank AC004473). However, regarding the promoter region that acts to control the transcription of said TPS3 gene, there is currently no report and/or invention referring to the identification of Arabidopsis TPS3 promoter that causes very strong, constitutive gene expression of a desired gene and maintains expression characteristics in root- and leaf-tissues in transgenic plants.

According to the present invention, therefore, a desired foreign gene and a terminator can be linked to the downstream site of Arabidopsis TPS3 promoter region obtained, and introduced into plant, whereby the desired gene can be expressed in the transgenic plant tissues. Thus, the promoter region can be utilized to afford biotic or abiotic stress-related transcription and expression of a desired gene for the improvement of plants and also to produce the biologically active substances in plant tissues.

SUMMARY OF THE INVENTION

The present invention provides isolated nucleic acid constructs that comprise a plant promoter operably linked to a heterologous gene for the highest expression level of a desired polypeptide in plant root tissue and leaf tissue. The plant promoter comprises stronger constitutive promoter, from Arabidopsis gene that encodes trehalose-6-phosphate synthase involved in trehalose metabolism, than CaMV 35S promoter. Also provided by the invention are expression vectors which include Arabidopsis TPS3 promoter operably linked to a heterologous gene that encodes a desired polypeptide.

The expression vectors can further comprise other components such as a selectable marker. The construct can also comprise an origin of replication sequence that functions in plant or other host cell. As preferred constructs of the invention, the plasmid pLES 99010 was deposited under Budapest treaty with the Korean Collection for Type Cultures (KCTC) located at #52, Oun-dong, Yusong-ku, Taejon 305–333, Republic of Korea with accession No. KCTC 0811BP on Jul. 1, 2000. Plasmid pLES 99011 was deposited under Budapest treaty with the Korean Collection for Type Cultures (KCTC) with accession No. KCTC 0812BP. Plasmid pLES 99014 was deposited under Budapest treaty with the Korean Collection for Type Cultures (KCTC) with accession No. KCTC 0813BP. Plasmid pLES 99015 was deposited under Budapest treaty with the Korean Collection for Type Cultures (KCTC) with accession No. KCTC 0814BP.

The present invention also provides a plant cell that contains a expression cassette that includes the Arabidopsis TPS3 promoter operably linked to a heterologous gene. The expression cassette can be integrated into the genome of the host cell or be present on an independently replicating plasmid. With said expression cassette, a gene manipulation of plants is possible, which enables the constitutive regulation of a desired gene expression in commercially important plants. A preferred plant cell is both dicot and monocot species.

The present inventors have conducted extensive researches and found a promoter capable of functioning in plant tissues, which enables very strong constitutive expression of desired genes, thereby completed the present invention.

BRIEF DESCRIPTION OF THE DRAWINGS

The patent or application file contains one color photograph. Copies of this patent or patent application publication with a color photograph will be provided by the Office upon request and payment of a reasonable fee.

FIG 4A is the quantitative activity of GUS reporter gene driven by Arabidopsis TPS3 promoters, while

DETAILED DESCRIPTION OF THE INVENTION

The present invention provides expression cassettes and vectors that are useful for constitutive expression of a desired polypeptide in plants at high levels. The promoter and vectors of the present invention are particularly suitable for the expression of proteins in plant hosts including soybean and rice, etc., for pathogen-resistance, environmental stress-tolerance or plant biofarming to obtain the high level of recombinant protein expression. Said promoter provides higher level of expression than that provided by CaMV 35S promoter.

General laboratory procedures required in this application can be found in Sambrook et al., Molecular cloning: A Laboratory Manual (2$^{nd}$ Ed.), Vol. 1-3, Cold Spring Harbor Laboratory, Cold Spring Harbor, N.Y., 1989. All technical and scientific terms used herein have the same meaning as commonly understood by the person having ordinary skill in the art to which this invention belongs. Although any methods and materials similar or equivalent to those described herein can be used for practicing or testing the present invention, the preferred methods and materials are described.

The term "nucleic acid" refers to a deoxyribonucleotide or ribonucleotides polymer in either single- or double-stranded form, and unless otherwise limited, encompasses known analogues of natural nucleotides that hybridize to nucleic acids in the manner similar to naturally occurring nucleotides. Unless otherwise indicated, a particular nucleic acid sequence includes the complementary sequence thereof.

The term "operably linked" refers to a functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can express genes that are not found within the native form of the cell. Recombinant cells can also express genes that are found in the native form of the cell, but wherein the genes are modified and re-induced into the cell by artificial means.

A "heterologous gene", as used herein, is the gene that originates from a foreign species or if originated from the same source, is the modified gene from its original form. Therefore, a heterologous gene operably linked to a promoter is from a source different from that from which the promoter was derived, or, if originated from the same source, is the modified promoter from its original form. For example, a trehalose-6-phosphate synthase gene promoter can be linked to a structural gene encoding a polypeptide other than native trehalose-6-phosphate synthase. Modification of the heterologous sequence may occur, e.g., by treating the DNA with a restriction enzyme to generate a DNA fragment that is capable of being operably linked to the promoter. Site-directed mutagenesis is also useful for modifying a heterologous sequence.

The promoter herein means a promoter capable of controlling expression of a protein in plant cells when a gene of protein of interest is fused to downstream of said promoter. Also, the promoter of the present invention may be further modified by ligating to other transcription-translation activating sequence.

An "expression cassette" is a nucleic acid construct, generated or synthetically, with nucleic acid elements that are capable of affecting expression of a structural gene in hosts that are compatible with such sequences. Expression cassettes include at least promoters and optionally, transcription termination signals. Typically, the expression cassette includes a nucleic acid to be transcribed and a promoter (e.g., a Arabidopsis TPS3 promoter). Additional factors helpful in effecting expression may also be used as described herein. For example, an expression cassette can also include nucleotide sequences that encode a signal sequence that directs secretion of an expressed protein from the host cell. To allow selection of transformed cells comprising the constructs, a selectable marker gene can be conveniently included in the expression vectors. A person having skill will recognize that this vector component can be modified without substantially affecting its function.

The practice of this invention involves the nucleic acid construct and the expression of genes in transformed plant cells. Molecular cloning techniques to achieve these ends are known in the art. A wide variety of cloning and in vitro amplification methods suitable for the construction of recombinant nucleic acids such as expression vectors are well known to persons of skill. Examples of these techniques and instructions sufficient to direct persons of skill through many cloning exercises are found in Jose M. Martinez-Zapater and Julio Salinas, *Arabidopsis protocols,* Humana Press.

The first aspect of the present invention is the nucleic acid construct comprising a nucleotide sequence (about 1.0 kb) of a promoter (SEQ ID NO: 1) from Arabidopsis trehalose-6-phosphate synthase (AtTPS3) gene. The identification of promoter having the desired characteristics can be accomplished in a number of ways. For example, genomic or cDNA libraries can be prepared from a known source of TPS3 gene such as Arabidopsis, *Myrothamnus flabellifolius* and yeast. A library from a given species is screened with oligonucleotide probes designed to contain sequences that are complementary to coding regions of other known genes. Alternatively, oligonucleotide probes can be designed on the basis of amino acid sequence information obtained from purified TPS3 protein. Oligonucleotide probes based on amino acid sequences can be degenerate or can be biased to favor the preferred codons of the source plant. Oligonucleotide primers can be designed for use in reverse transcription-polymerase chain reaction (RT-PCR) to amplify PCR fragments for cloning and sequencing. The sequences of the PCR fragments can be compared with known coding regions of desired genes to identify corresponding clones. As an example, the cDNA of pathogen responsive gene is obtained by RT-PCR, using the total RNA prepared from pathogen-infected plant tissue and gene-specific primers.

The cDNA then is used as bait for isolating the promoter region using genomic restriction libraries from the plant tissue in consecutive PCR reactions with nested primers. The PCR amplification products are cloned and sequenced. The promoter region may be native or homologous to the host or foreign or heterologous to the intended host. The term "foreign" is intended to mean that the transcriptional initiation region is not usually found in the plant host into which it is introduced. The Arabidopsis trehalose-6-phosphate synthase 1 gene (Blazquez et al., 1998. *The Plant Journal* 13(5): 685–689) or *Saccharomyces cerevisiae* trehalose-6-phosphate synthase 2 gene (De Virgilio et al., 1993. *Eur J. Biochem.* 212: 315–323) is a particular example of a gene which one can obtain a promoter that is useful in the present invention. Said construct may be composed of base sequences derived from SEQ ID NO: 1 with some bases deleted, inserted or substituted, so far as the resulting sequences effectively retain said promoter and expression regulatory activities. In addition, these sequences having some bases deleted, inserted or substituted are essentially the same in function as said base sequences, so far as they effectively retain said promoter activity.

The nucleotide sequence of a most preferred promoter is shown in SEQ ID NO: 1. As shown, the promoter is inserted into the XbaI site of pLES99014 expression vector. The TATA box sequence of the promoter is at nucleotides 918–923. To facilitate insertion of a gene to be expressed downstream of the promoter, a SmaI site is present in the pLES99014 sequence just 3' of the XbaI site.

The nucleotide sequence of the desired promoter fragments can be synthesized by well-known techniques as described in the technical literature (Carruthers et al., 1982. Cold Spring Harbor Symp. *Quant. Biol.* 47:411–418). One can be obtained double stranded DNA fragments either by synthesizing the complementary strand and annealing the strands together under appropriate conditions.

The second aspect of the present invention is an expression cassette or a vector integrating expression cassette to be used as an expression vector. The plasmid comprising the promoter of the invention is constructed to have a restriction enzyme site for excising or inserting a desired gene downstream of the promoter of the present invention. The desired gene may be heterologous in relation with said promoter. The plasmid also comprises chimeric gene(s) which is prepared by ligating desired structural gene(s) to said promoter for the expression of desired protein(s) in plant root and leaf tissues, and also which is autonomously replicating, inheritable and the like. Since the promoter of the present invention enables the expression of a desired protein in plant root and leaf tissue, GUS reporter gene in the present invention can be excised and replaced by a desired gene capable of enhancing either resistance against biotic/abiotic stresses or the production of biologically active substances in transgenic plants.

A nucleotide sequence of interest can be inserted downstream from and under the control of the promoter of the present invention. The nucleotide sequence of interest provides for modification of phenotypic characteristics by altering the production of an endogenous product or by encoding a functionally novel gene product. The nucleotide sequence may have any open reading frame encoding an enzyme or a sequence complementary to a genomic sequence, where the genomic sequence may be an open reading frame or any other sequence where the complementary sequence inhibits transcription, messenger RNA processing. The nucleotide sequence of interest may be synthetic, of natural origin, or combinations thereof. Depending upon the nature of the nucleotide sequence of interest, it may be desirable to synthesize the sequence with plant-preferred codons.

The vectors also comprise selectable marker genes to allow selection of host cells bearing the desired construct. These genes encode a protein necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as kanamycin and hygromycin. A series of selectable markers are known to those of skill in the art and are described for instance in Sambrook et al. Construction of preferable vectors containing one or more of the above mentioned components employs standard techniques as described in the reference cited above.

A number of plant host cells can be used with the vectors of the invention. Examples of such plants include soybean, tomato, potato, tobacco, rice, maize, wheat, barley, strawberry, and rapeseed. These examples are illustrative rather than limiting. Depending upon the host cell used, transformation will be done using standard techniques appropriate to such cells.

The promoter of the present invention is useful for expression of any desired protein in plant host cells at very high levels. The protein may be homologous to plant host cell, or preferably, are heterologous to the host cell. For example, one can express mammalian, fungal, and plant proteins at very high levels using said promoter. Exemplary proteins that one can express using said promoter includes trehalose-6-phosphate synthase, ABA-responsive element binding factor (ABF), pathogen-responsive genes (R genes), carbohydrate metabolizing enzymes, carotene synthesizing enzymes, flavonoids synthesizing enzymes, growth hormones, insulin, interleukins, colony stimulating factors, and like. The above listed enzymes are exemplary, not exclusive, as said promoter of the invention is useful for obtaining transcription of any nucleic acid expression that is operably linked to said promoter. As host plant cells to which said promoter is introduced, the plant root and leaf tissues is preferred wherein the expression of a foreign gene is specifically elevated. Therefore, the transduction of expression vector harboring said promoter into plant cells with regeneration potency provides effective means to engineer into such grain producing plants as rice such commercially and agriculturally desirable traits conferring biotic/abiotic resistance and/or high plant productivity.

Provided are the constructs of the present invention for obtaining transgenic plants that have either constitutive resistance to infection and stress or enhancing production of biologically active substances. Particularly, the plant cells transformed with the construct of the present invention can be regenerated by conventional plant tissue culture techniques (Jose M. Martinez-Zapater and Julio Salinas, *Arabidopsis protocols*, Humana press, 1998). Of considerable interest, the expression of the DNA sequences of interest is constitutively expressed at the site of the stress, particularly root and leaf tissue. The constructs provide for modulation of expression of endogenous products as well as production of exogenous products in the plant. A DNA construct is introduced into a plant cell host for integration into the genome and transcription. In this manner, the high level of RNA and, as appropriate, polypeptides can be achieved at lifetime. Confirmation of very strong, constitutive expression of a desired gene can be achieved by transforming plants, or plant tissue with said invention.

Trehalose-6-phosphate synthase 3 (TPS3) is catalyzing the synthesis of α-D-glucopyranosyl α-D-glucopyranoside (the non-reducing disaccharide trehalose) from glucose-6-phosphate and uridine-diphosphoglucose. The absence of reducing ends renders trehalose highly resistant to heat, pH and Maillard's reaction (a reaction between carbohydrates and amino acids that results in discoloration during the processing of potatoes). Moreover, trehalose has a strong stabilizing effect on biological structures, forming a glass-like structure after dehydration. Because of these characteristics, there has been a growing interest in trehalose metabolism as a means of engineering environmental stress tolerance in crops and in trehalose as a useful stabilizing agent to preserve dried or frozen foodstuffs and an additive in cosmetics and pharmaceuticals.

Of the gene of TPS1, the complete sequence of cDNA as derived from Arabidopsis has been reported [Blazquez et al., *The Plant Journal* (1998) 13:685–689]. However, regarding the promoter region which functions to control the transcription of such TPS3 gene, there was no report yet referring to the isolation of the promoter gene and its utilization thereof. Having the above knowledge, the present invention can be utilized for the expression of foreign genes into agriculturally important plants. The construct of the present invention is activated within 15 min after expression and remains active. Therefore, the rapidity and strength of induction of gene expression provided by the construct of the present invention are particularly advantageous where it is desired to trigger or greatly enhance plant resistance responses to pathogen, to increase the effectiveness of mechanisms that protect against abiotic stresses (e.g., environmental stress responsive enzymes) or to produce biologically active substances (e.g., enzymes producing biologically active materials). In this manner, the DNA sequences of interest are constitutively expressed at transgenic plant root and leaf tissue, which specificity may avoid potential deleterious effects to the plant which constitutive expression of such sequences may cause.

The desired effects on plant resistance may be achieved by the expression of genes for resistance to fungi or nematodes, for example. Examples of genes which may be expressed under the regulatory control of the constructs of the present invention for enhanced disease resistance are described in Hammond-Kosack, K. B. and Jones, J. G. D. ("Plant disease resistance genes", *Annu. Rev. Plant Physiol.* (1997) 48:575–607).

The ability to achieve a high-level of transgene expression is also of considerable importance in "molecular farming", wherein plants are used to produce industrial or pharmaceutical polypeptides and other biopolymers that are foreign to plants. It is also expected that the promoter of the present invention will be advantageous for use in the well-known gene constructs to develop sensitive and rapid cell-based screens for environmental and agricultural monitoring.

With attempt to isolate the promoter region of TPS3 gene that is actively expressed in plant root and leaf tissues, thereby utilizing it in the improvement of plant disease resistance, environmental stress tolerance, or in the production of biologically active substances in plant root tissues and leaf tissues, the present inventors have studied to attain this object, and, as a result, have completed the present invention.

The following examples illustrate the preparation of the expression cassette, whose DNA sequence comprises a regulatory sequence for strong, particularly stronger than CaMV35S promoter, constitutive gene expression in plant root and leaf tissue. The introduction of the sequence in a plasmid is also illustrated in that a transformation of plant cells is possible. In addition, the regeneration of transgenic plants and the investigation of the function of the expression cassette in transgenic plants are shown. One skilled in the art will recognize that substitutions and alterations may be made in the components, conditions, and procedures presented herein without departing from the scope or intention of the protocol.

EXAMPLES

The following examples are offered by way of illustration and not by way of limitation.

Example 1

Isolation of the Promoter

1) Isolation of Total RNA from *Arabidopsis thaliana*

Ten grams of leaves from a month old *Arabidopsis thaliana* were frozen in liquid nitrogen and ground in mortar and pestle to a fine powder. The grounded material was transferred to a chilled Corex tube to which was added 10 ml of ice cold extraction buffer containing 200 mM Tris at pH 7.0, 5 mM EDTA, 0.1 M LiCl and 1% SDS followed by heating at 65° C. for 10 min. The suspension was centrifuged at 20° C. for 20 min at 15,000 rpm. The supernatant fraction was collected. Total RNA was precipitated by the addition of 0.5 volumes of phenol and chloroform followed by 2 M LiCl treatment. After dissolved with water, total RNA was precipitated with the addition of two volume of ethanol at −20° C. followed by centrifugation at 12,000 rpm, 4° C., for 10 min. All glasswares and solutions were previously treated with 0.1% diethylpyrocarbonate and sterilized.

2) Isolation of mRNA from *Arabidopsis thaliana*

Poly-A$^+$ RNA was isolated and purified with Oligotex™ mRNA Midi kit (QIAGEN, Germany), according to the manufacturer's directions. Total RNA was loaded to the Oligotex™ column equilibrated with 2× binding buffer after total RNA was heated at 65° C. for 5 minutes. The Oligotex™ column was twice washed with 0.5 ml of the washing buffer followed by 20 μl of the elution buffer. Poly-A$^+$ RNA obtained was precipitated with 2.5 volume of absolute ethanol at −20° C. and centrifuged at 12,000 rpm, 4° C. for 10 min. Poly-A$^+$ RNA precipitated was dissolved with 20 μl of TE buffer containing 10 mM Tris-Cl, pH 8.0, and 1 mM EDTA after washing with 70% ethanol. Poly-A$^+$ RNA concentration was determined spectrometrically at 260 nm. All procedures were performed with the operator wearing surgical rubber gloves to minimize nuclease contamination of the mRNA preparation.

3) Synthesis and Cloning of cDNA from *Arabidopsis thaliana* cDNA library from *Arabidopsis thaliana* was constructed with Uni-ZAP™ cDNA library kit (Stratagene, USA), according to the manufacturer's manual. The first-strand cDNA was synthesized from the reaction mixtures of 5 μg of poly-A$^+$ RNA, oligo (dT)$_{12-18}$, murine reverse transcriptase, dNTP, BSA, and DTT. In order to synthesize double-stranded cDNA, the first-strand cDNA synthesized was blunted at cDNA termini with the addition of *E. coli* RNase H, *E. coli* DNA polymerase I, and dNTP at 16° C. for 3 h followed by treating the dNTP mixture with Pfu DNA polymerase at 65° C. for 10 min.

4) Ligation of cDNA into Uni-ZAP™ ZAP Vector

The termini of cDNA synthesized were ligated to the EcoRI adapter for the insertion of cDNA to the vector. cDNA synthesized was reacted with the addition of EcoRI adapter, ATP, T4 DNA ligase at 12° C. overnight followed by further reaction with the addition of T4 DNA kinase and ATP at 37° C. for 30 min for the ligation of the EcoRI adapter. cDNA was purified with Sephacryl S-500 spin column, and its signal was confirmed on 1.0% agarose gel electrophoresis. Above 1 kb of cDNA fractions was used for further experiments. The insertion of cDNA was resulted from the reaction of the mixtures containing 200 ng of cDNA, 1 μg of vector DNA (Stratagene) and T4 DNA ligase at 4° C. for 48 h.

5) Construction and the Amplification of cDNA Library

The Uni-ZAP™ vector DNA was packaged by using Gigapack II packaging extract containing phage ghost (Stratagene). The packaging extract was reacted by the addition of recombinant vector at 22° C. for 2 h. The reaction solution was adjusted up to 500 μl of final volume with SM buffer supplemented with 10 μl of chloroform, and was immediately used or stored at 4° C. until it will be used. Total plaque-forming unit (pfu) of recombinant cDNA library was obtained from $10^{-2}$–$10^{-6}$ fold-diluted solution. 200 μl of *E. coli* strain XL1-Blue MRF' were incubated with cDNA library at 37° C. for 15 min, and plated to reach $10^6$ pfu on plate of 150 mm in diameter. The plate supplemented with 5 ml of SM buffer was incubated at 4° C. overnight after reacted the plate at 37° C. for 12 h. The supernatants was obtained from the reacted SM buffer by centrifuging at 12,000 rpm for 10 min, and stored with 100 μl of chloroform at −4° C. The plaque-forming unit was calculated as described in the above.

6) Polymerase Chain Reaction for Promoter Cloning

A large-scale total phagemid DNA preparation was also made for PCR amplification to isolate partial cDNA piece for further library screening. Phage stock containing total cDNA library was transferred in a form of plasmid from *E. coli* XL1-B MRF' cell into XL1-B SOLR cell via a ExAssist helper. Using this phagemid prep as a template, PCR was performed in 30 cycle of 95° C./30 sec, 50° C./30 sec, 72° C./30 sec with the cocktail mixtures containing 5 μl 10× Taq buffer, 2 μl 25 mM $MgCl_2$, 2 μl 10 pmol each primer, 4 μl 2 mM dNTPs, 0.25 μl cDNA pool, 33.75 μl water by using combinations of vector primers and two degenerate primers.

7) Selection of cDNA Library

*E. coli* strain XL1-Blue MRF' as a host cell for phage adhesion was cultured in 50 ml LB medium with 20% maltose, 0.5 ml of 1 M $MgSO_4$ and 50 μg/ml tetracycline. Cell cultures were suspended in 10 MM $MgSO_4$ to make O.D. 0.5 at $A_{600}$. After cultured *E. coli* strain XL1-Blue MRF' with cDNA library at 37° C. for 30 min, the culture mixed with 3 ml of 0.7% LB agar was further incubated on 1.5% LB agar plate at 37° C. for 12 h. $5×10^4$ cells were used in the first selection, and $1×10^3$ in second selection. The plates formed phage plaque were stayed at 4° C. for 1 h, and replicated with Hybond-C membrane (Amersham, USA).

8) PCR Cloning of 1.0 Kb TPS3 Gene Promoter

Figure 1A:
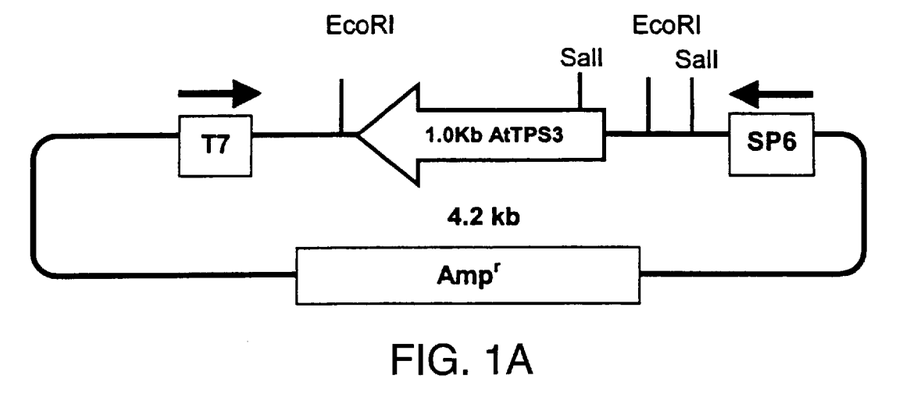
FIG. 1A shows a schematic representation of the plasmid pLES99010, containing 1.0 kb Arabidopsis TPS3 promoter (SEQ ID NO: 1)

For the cloning of the TPS3 promoter, gene specific primer set was designed by based on *Arabidopsis thaliana* BAC T13D8 genomic sequence that contains a trehalose-6-phosphate synthase homolog, T13D8.4. About 1.0 Kb of TPS3 promoter was amplified by the Polymerase Chain Reaction (PCR) from genomic DNA using T13P3 (5'-TCCAAATGATTTTGACCCCAT-3') [SEQ ID NO: 3] and T13P5-2 (5'-GTGTTCATTTGATAGAGTCTA-3') [SEQ ID NO: 4] primers. The PCR reaction mixtures contained 500 ng of genomic DNA 5 ul of 10× Taq polymerase buffer (pH 8.0) 1 mM of $MgCl_2$, 200 μm of dNTPs, 20 pmole of each primer, and 5U of Taq polymerase. The reaction was hot started and amplified as the following conditions: 1 cycle of 95° C. for 5 minute as post-denaturation; 30 cycles of 95° C. for 30 seconds, 50° C. for 30 seconds, 72° C. for 1 minute; 1 cycle of 72° C. for 10 minutes as post-extension in a Perkin-Elmer 9800 thermocycler. The amplified major product from the PCR reaction was gel-purified using QIAquick gel extraction kit (Qiagen, USA) and subsequently cloned into the pGEM-T easy vector (Promega, USA), which yields the plasmid construct pLES99010 (FIG. 1A), according to the manufacturer's guide and sequenced. One clone that contained 1 kbp upstream sequence [SEQ ID NO: 1] was designated as the 1 kb TPS3 promoter.

9) PCR Cloning of 2.0 Kb TPS3 Gene Promoter

Figure 1B:
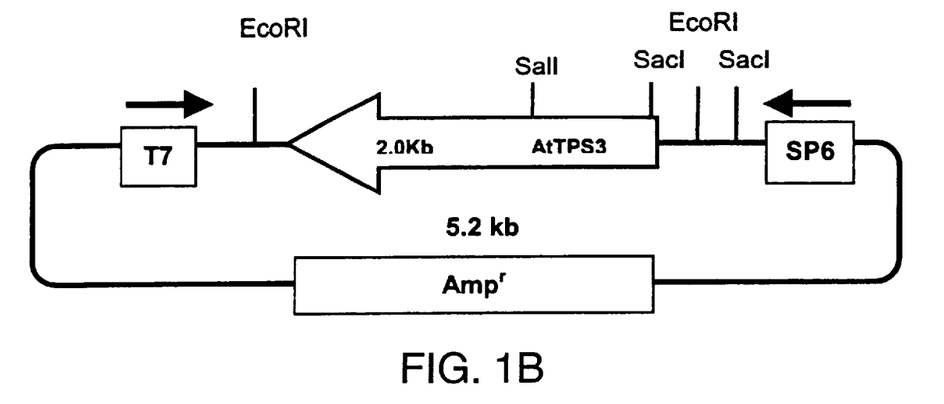
FIG. 1B shows the plasmid pLES99011 containing 2.0 kb Arabidopsis TPS3 promoter (SEQ ID NO: 2) for *E. coli* transformation.

About 2.0 Kb of TPS3 promoters were amplified by the PCR reaction from genomic DNA using the gene specific primer set, T13P3 (5'-TCCAAATGATTTTGACCCCAT-3') [SEQ ID NO: 3] and T13P5-1 (5'-CGACGGCATTAACATAAACC-3') [SEQ ID NO: 5]. The PCR reaction was performed using the same buffer and amplification conditions as in the above. The amplified major product from the PCR reaction was cloned into the pGEM-T easy vector (Promega, USA), which yields the plasmid construct pLES99011 (FIG. 1B), according to the manufacturer's guide and sequenced. One clone that contained 2 kbp upstream sequence [SEQ ID NO: 2] was designated as the 2 kb TPS3 promoter.

Example 2

Construction of the Expression Vectors

Figure 2A:
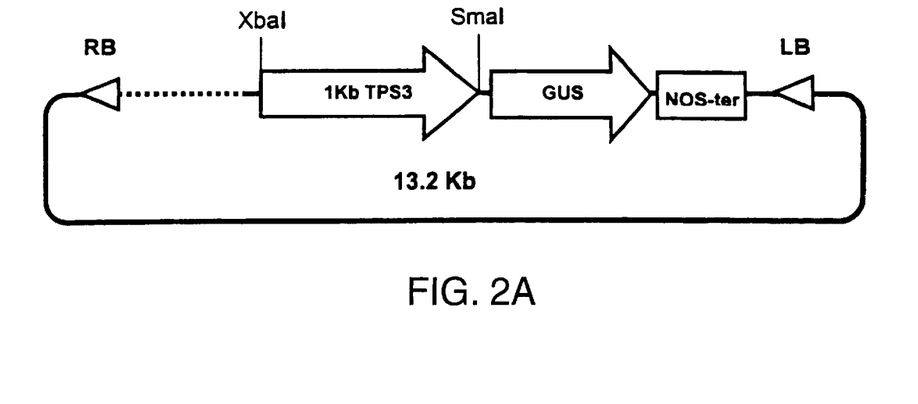
FIG. 2A shows a schematic representation of the plasmid pLES99014, containing 1.0 kb Arabidopsis TPS3 promoter (SEQ ID NO: 1)
Figure 2B:
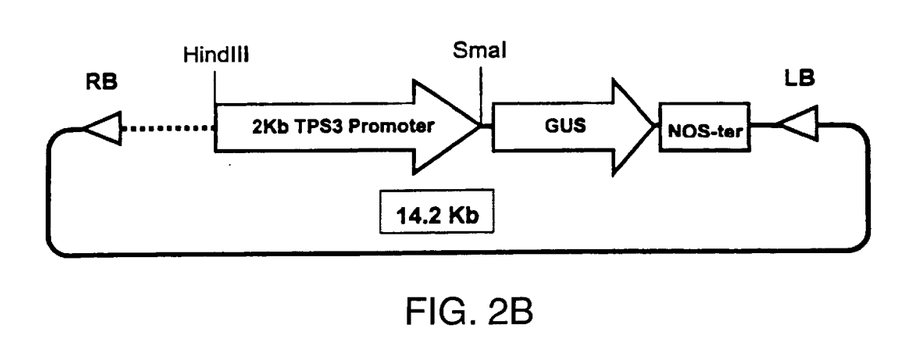
FIG. 2B shows the plasmid pLES99015, containing 2.0 kb Arabidopsis TPS3 promoter (SEQ ID NO: 2) for plant transformation.

A) Preparation of the TPS3 Promoter-GUS Reporter Gene Constructs and Expression Vectors A DNA fusion construct of the promoter with a reporter gene encoding β-glucuronidase (GUS) was made as follows. For a convenient cloning into the binary vector pBI101, the plasmids pLES99010 and pLE99011 were digested with EcoRI and subcloned into the EcoRI site of pBluescript KS. These clones were named as pLES99012 and pLES99013, respectively The pLES99012 was digested with XbaI and EcoRV to generate the 1.0 Kb TPS3 promoter, and subsequently subcloned into the XbaI/SmaI sites of pBI101.2, yielding the pLES99014 expression vector (FIG. 2A). For the pLES99015 expression vector construct (FIG. 2B), pLES99013 was digested with HindIII ad SinaI, and subcloned into HindIII/SmaI sites of pBI101.2. The fidelity of all constructs was verified by sequencing. The vectors, pLES99014 and pLES99015, containing the TPS3 promoter/GUS gene fusion were transformed into *Agrobacterium tumefaciens* strain GV3101, respectively, by the method of Jose M. Matinez-Zapater and Julio Salinas, Arabidopsis protocols (Humana press, 1998).

Example 3

Generation of Transgenic Plants and the Evaluation of TPS3 Promoter Function in Transformed Plants A) Transformation of Arabidopsis Plants The vectors, pLES99014 and pLES99015, were introduced into *Arabidopsis thaliana* (L.) Heynh., ecotype Col-0 by Agrobacterium-mediated vacuum infiltration method according to Jose M. Martinez-Zapater and Julio Salinas, *Arabidopsis protocols* (Humana press, 1998). For a selection of kanamycin resistant-positive transformants, $T_1$ seeds were surface sterilized with 70% ethanol followed by 50% household bleach with Tween 20, and then washed four times in sterilized water. Seedlings were grown in Murashige and Skoog (MS) medium agar plates containing 1% sucrose and 50 mg/ml kanamycin and placed in either a vertical or horizontal position. Plants were grown at 22 to 24° C. under 16 hours of light period. The transgenic lines of one copy insertion were verified using the RT-PCR method with $T_2$ seedlings, and their homozygote progenies were assayed for the GUS activity.

B) GUS Analysis

Positive transformants grown on the vertical plate were assayed for TPS3 promoter function by staining transformed plantlets with 5-bromo-4-chloro-3-indole-β-D glucuronide (X-Gluc) at 1 hour or daytime points. Transformed seedlings or plantlets were immersed in the GUS reaction buffer (2 mM 5-bromo-4-chloro-3-indole-β-D glucuronide (X-Gluc), 1% dimethylformamide, 0.1 mM potassium ferricyanide, 0.1 mM potassium ferrocyanide, 1 mM EDTA, 50 mM sodium phosphate buffer, pH 7.0) followed by brief vacuum infiltration. Tissues were incubated at 37° C. for 1 to 3 hours.

Figure 3:
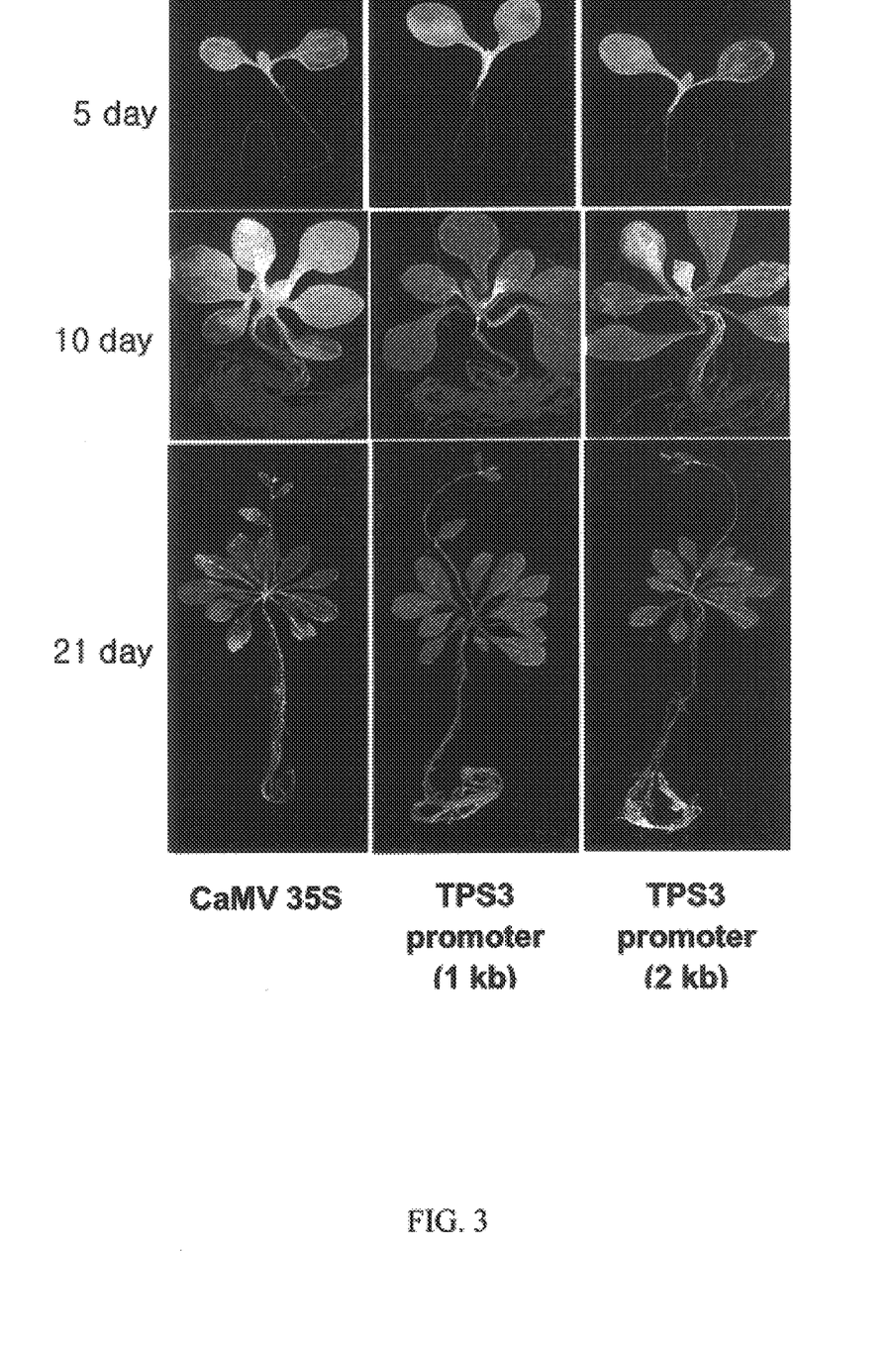
FIG. 3 shows an expression of GUS reporter gene activity driven by Arabidopsis TPS3 promoter or CaMV 35S promoter. Developing seedlings grown on vertical plate for 5, 10, and 21 days, respectively, were incubated in X-Gluc solution for 1 to 3 hours.
Figure 4A:
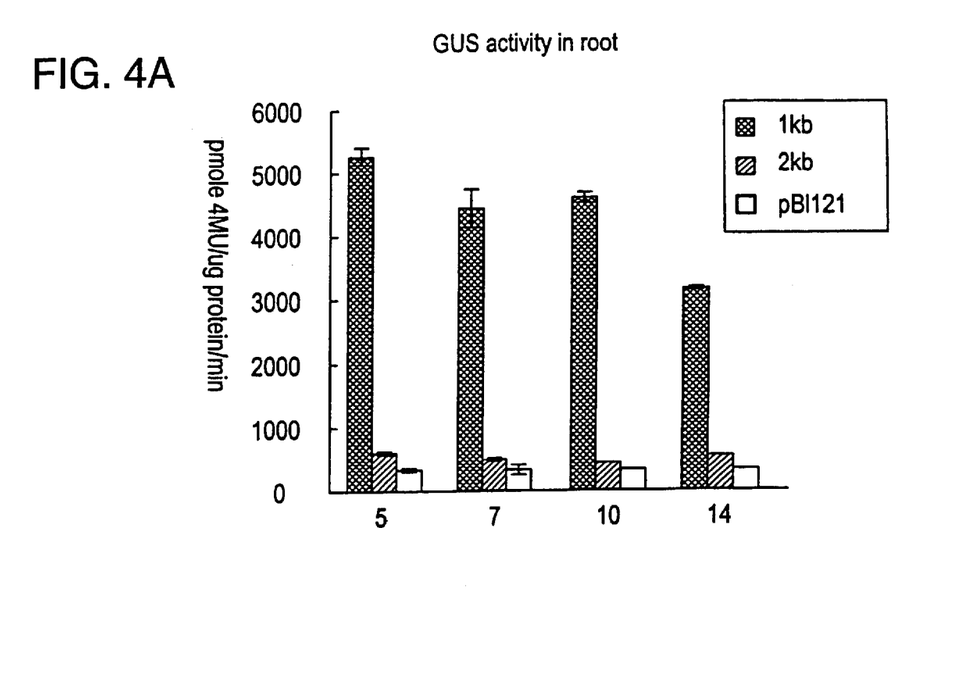
Figure 4B:
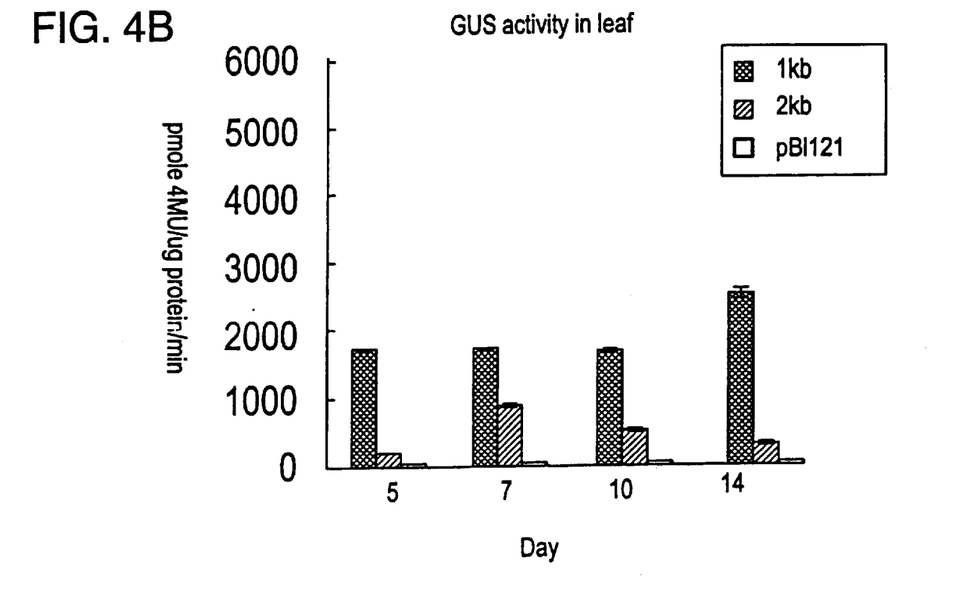
FIG. 4B shows the quantitative activity driven by the CaMV 35S promoter. Developing seedlings grown on vertical plate for 5, 7, 10, and 14 days, respectively, were assayed with 4-MUG solution.

After incubation, seedlings or plantlets were destained with washes of 1 hour using 70% ethanol and more than 48 hours using 100% ethanol for better visualization, and photographed (FIG. 3).

Five kanamycin resistant Arabidopsis lines were analyzed for induction of GUS activity. Three lines showed a strong induction of GUS expression 15 min. post incubation, two lines showed a mild induction. Strength of induction was determined by visual inspection of relative color intensity after GUS staining.

REFERENCES

Goddijn and Van Dun, *Trend in Plant Science.* (1999)48: 315–319.

Holmstroem, *Nature* (1996) 379: 683–684.

Blazquez et al., *Plant J.* (1998) 13: 685–689.

Bell et al., *J Biol. Chem.* (1998) 273: 33311–33319.

What is claimed is:

1. An isolated promoter that is functional in plants comprising the nucleotide sequence as shown in SEQ ID NO: 1.

2. A promoter that is functional in plants comprising the nucleotide sequence as shown in SEQ ID NO: 2.

3. A plasmid comprising the promoter according to claim 1.

4. A plasmid comprising the promoter according to claim 2.

5. A chimeric DNA construct comprising the plant promoter of claim 1 operably linked to a heterologous nucleic acid encoding a desired polypeptide.

6. A chimeric DNA construct comprising the plant promoter of claim 2 operably linked to a heterologous nucleic acid encoding a desired polypeptide.

7. A plasmid comprising the chimeric DNA construct according to claim 5.

8. A plasmid comprising the chimeric DNA construct according to claim 6.

9. A microorganism containing the plasmid according to claim 3, wherein said microorganism is *E. coli* DH5@/pLES9901 (deposited as KCTC 0811BP).

10. A microorganism containing the construct according to claim 7, wherein said microorganism is *Agrobacterium tumefaciens* GV3101/pLES99014 (deposited as KCTC 0813BP).

11. A microorganism containing the plasmid according to claim 4, wherein said microorganism is *E. coil* DH5@/pLES99011 deposited as KCTC 0812BP.

12. A microorganism containing the construct according to claim 8, wherein said microorganism is *Agrobacterium tumefaciens* GV3101/pLES99015 deposited as KCTC 0814BP.

* * * * *